US00PP12477P2

(12) United States Plant Patent
Trees

(10) Patent No.: US PP12,477 P2
(45) Date of Patent: Mar. 19, 2002

(54) GERANIUM PLANT NAMED 'BALFANCARDIM'

(75) Inventor: Scott C. Trees, Shell Beach, CA (US)

(73) Assignee: Ball FloraPlant, A division of Ball Horticultural Co., West Chicago, IL (US)

( * ) Notice: Subject to any disclaimer, the term of this patent is extended or adjusted under 35 U.S.C. 154(b) by 0 days.

(21) Appl. No.: 09/822,010

(22) Filed: Mar. 31, 2001

(51) Int. Cl.[7] ..... A01H 5/00
(52) U.S. Cl. ..... Plt./330
(58) Field of Search ..... Plt./330

(56) References Cited

U.S. PATENT DOCUMENTS

PP5,930 P * 4/1987 Schumann ..... Plt./330

* cited by examiner

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Geranium plant named 'Balfancardim', characterized by its upright and mounded growth habit; freely basal branching habit; dark green leaves with darker green zonation pattern; and dark red-colored semi-double flowers.

1 Drawing Sheet

BACKGROUND OF THE INVENTION

The present invention relates to a new and distinct cultivar of Geranium plant, botanically known as *Pelargonium*× *hortorum*, and hereinafter referred to by the name 'Balfancardim'.

The new Geranium is a product of a planned breeding program conducted by the Inventor in Arroyo Grande, Calif. The objective of the breeding program was to develop new cultivars with freely-branching and vigorous growth habit, dark green-colored foliage, umiform flowering, and interesting flower and foliage colors.

The new Geranium originated from a cross made by the Inventor of the proprietary *Pelargonium*×*hortorum* selection 8806-112 as the female, or seed, parent with the proprietary *Pelargonium*×*hortorum* selection 6494-26 as the male, or pollen, parent. The cultivar 'Balfancardim' was discovered and selected by the Inventor as a flowering plant within the progeny from this cross in a controlled environment in Arroyo Grande, Calif., in 1998.

Asexual reproduction of the new cultivar by terminal cuttings taken at Arroyo Grande, Calif., has shown that the unique features of this new Geranium are stable and reproduced true to type in successive generations of asexual reproduction.

SUMMARY OF THE INVENTION

The following traits have been repeatedly observed and are determined to be the unique characteristics of 'Balfancardim'. These characteristics in combination distinguish 'Balfancardim' as a new and distinct cultivar:

1. Upright and mounded growth habit.
2. Freely basal branching habit.
3. Dark green leaves with darker green zonation pattern.
4. Dark red-colored semi-double flowers.

Plants of the new Geranium differ primarily from plants of the female parent selection in flower color and flower form as plants of the parent selection have coral-colored single flowers. Plants of the new Geranium differ primarily from plants of the male parent selection in foliage color as plants of the parent selection have medium green-colored leaves.

The new Geranium can be compared to the cultivar 'Tango', disclosed in U.S. Plant Pat. No. 5,933. However, in side-by-side comparisons conducted in Arroyo Grande, Calif., plants of the new Geranium differ from plants of the cultivar 'Tango' in the following characteristics:

1. Plants of the new Geranium have shorter internodes than plants of the cultivar 'Tango'.
2. Plants of the new Geranium have shorter peduncles and pedicels than plants of the cultivar 'Tango'.
3. Plants of the new Geranium have larger leaves than plants of the cultivar 'Tango'.
4. Plants of the new Geranium have smaller flower umbels than plants of the cultivar 'Tango'.
5. Flower color of the new Geranium is darker red than flower color of the cultivar 'Tango'.

The new Geranium can be compared to the cultivar, 'Tango Dark Red', not patented. However, in side-by-side comparisons conducted in Arroyo Grande, Calif., plants of the new Geranium differ from plants of the cultivar 'Tango Dark Red' in the following characteristics:

1. Plants of the new Geranium have longer peduncles than plants of the cultivar 'Tango Dark Red'.
2. Plants of the new Geranium have larger leaves than plants of the cultivar 'Tango Dark Red'.
3. Plants of the new Geranium have larger flowers than plants of the cultivar 'Tango Dark Red'.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of a typical flowering plant of 'Balfancardim'. Flower and foliage colors in the photograph may differ slightly from the color values cited in the detailed botanical description which accurately describe the colors of the new Geranium.

DEATILED BOTANICAL DESCRIPTION

The cultivar 'Balfancardim' has not been observed under all possible environmental conditions. The phenotype may vary somewhat with variations in environment such as temperature and light intensity, without, however, any variance in genotype. The following observations, measurements and comparisons describe plants grown 10-cm pots in West Chicago, Ill., under commercial practice in a polycarbonante-covered greenhouse with day temperatures about 20 to 22° C., night temperatures about 18 to 20° C. and light levels about 2,500 to 3,000 foot-candles. Plants used for the photograph and description were about 8 to 10 weeks from planting rooted cuttings. In the following description, color references are made to The Royal Horticulural Society Colour Chart except where general terms of ordinary dictionary significance are used.

Botanical classification: *Pelargonium×hortorum* cultivar 'Balfancardim'.

Parentage:

*Female parent.*—Proprietary *Pelargonium×hortorum* selection 8806-112.

*Male parent.*—Proprietary *Pelargonium×hortorum* selection 6494-26.

Propagation:

*Type cutting.*—Terminal cuttings.

*Time to initiate roots.*—About 7 days at 18° C.

*Time to develop roots.*—About 21 days at 18° C.

*Root description.*—Fibrous, freely branching.

Plant description:

*General appearance.*—Upright and mounded growth habit. Appropriate for 10-cm and larger containers.

*Crop time.*—Starting with a rooted cutting, about 8 to 10 weeks are required to produced a finished flowering plant in 10-cm container.

*Growth and branching habit.*—Vigorous and freely basal branching with about 6 lateral branches at the base. Pinchng, that is, removal of terminal apices, is typically not required.

*Plant height* (*to top of foliage*).—About 10.5 cm.

*Plant width.*—About 19.7 cm.

*Lateral branches.*—Length: About 13 cm. Internode length: About 1.1 cm. Color: 143C.

*Foliage description.*—Leaves simple, generally symmetrical, abundant, opposite. Quantity of leaves per lateral branch: About 14. Length: About 5.4 cm. Width: About 9.1 cm. Shape: Reniform. Apex: Rounded. Base: Cordate. Margin: Crenate. Venation: Palmate. Texture: Smooth; slightly pubescent on upper surface and along veins of lower surface. Color: Young foliage, upper surface: 147A; zonation pattern, darker than 147A in color and located on the outer half of the leaf. Young foliage, lower surface: 147B. Fully expanded foliage, upper surface: Darker than 147A; zonation pattern, much darker than 147A in color, about 2.5 cm in width, and located on the outer half of the leaf. Fully expanded foliage, lower surface: 147A. Venation, upper and lower surfaces: 146B. Petiole: Length: About 5 cm. Diameter: About 3 mm. Color: 146A.

Flower description:

*Flower arrangement and type.*—Dark red-colored flowers arranged in hemispherical umbels arising from apical leaf axils. Umbels displayed above the foliage. At full flowering, usually about 2 open umbels and about 3 developing umbels per plant. Flowers semi-double and rounded in shape. Umbels persistent. Flowers not fragrant.

*Flowering season.*—Year-round under greenhouse conditions. In the garden, flowering is continuous from spring until fall.

*Umbels.*—Number of flowers per umbel: About 9. Diameter: About 7.4 cm. Height: About 5.1 cm. Flower diameter: About 4.3 cm.

*Flower buds.*—Length: About 1.6 cm. Diameter: About 1 cm. Shape: Spherical to ovoid. Color: Before showing color, 144A; when showing color, closest to 45B.

*Petals/petaloids.*—Quantity: About 6 petals and about 2 to 4 petaloids per flower. Petaloids variable in size and shape. Arrangement: Imbricate. Petal length: Upper petals: About 2.6 cm. Lower petals: About 2.4 cm. Petal width: Upper petals: About 1.8 cm. Lower peals: About 2.2 cm. Petal shape: Obovate. Petal/petaloid apex: Rounded. Petal/petaloid base: Attenuate. Petal/petaloid margin: Entire. Petal/petaloid texture: Smooth. Petal/petaloid color: Upper surface: 45B, venation towards base of upper petals, 45A. Lower surface: Between 39A and 40A; venation on upper petals, 58A, venation on lower petals, 45B.

*Sepals.*—Quantity: About 5, not imbricate. Length: About 9 mm. Width: About 3 mm. Shape: Ensiform. Apex: Narrowly acute. Margin: Entire. Texture: Velvety. Color, upper and lower surfaces: Mostly 144A with 187A towards base.

*Peduncle* (*umbel stem*).—Length: About 12.5 cm. Angle: Erect. Strength: Strong. Texture: Velvety. Color: 146A overlain with 187A.

*Pedicel* (*individual flower stem*).—Length: About 2.4 cm. Angle: Erect. Strength: Strong. Texture: Velvety. Color: 137A.

*Reproductive organs.*—Androecium: Anther quantity: About 5. Anther length: About 2 mm. Anther color: 70B. Pollen amount: Moderate. Pollen color: 167A. Gynoecium: Pistil quantity: One. Pistil length: About 8 mm. Stigma shape: Five-parted, star-shaped. Stigma color: 53B. Style length: About 4 mm. Style color: 53A.

*Seed.*—Not observed.

Disease resistance: Resistance to pathogens common to Pelargonium has not been observed.

It is claimed:

1. A new and distinct cultivar of Geranium plant named 'Balfancardim', as herein illustrated and described.

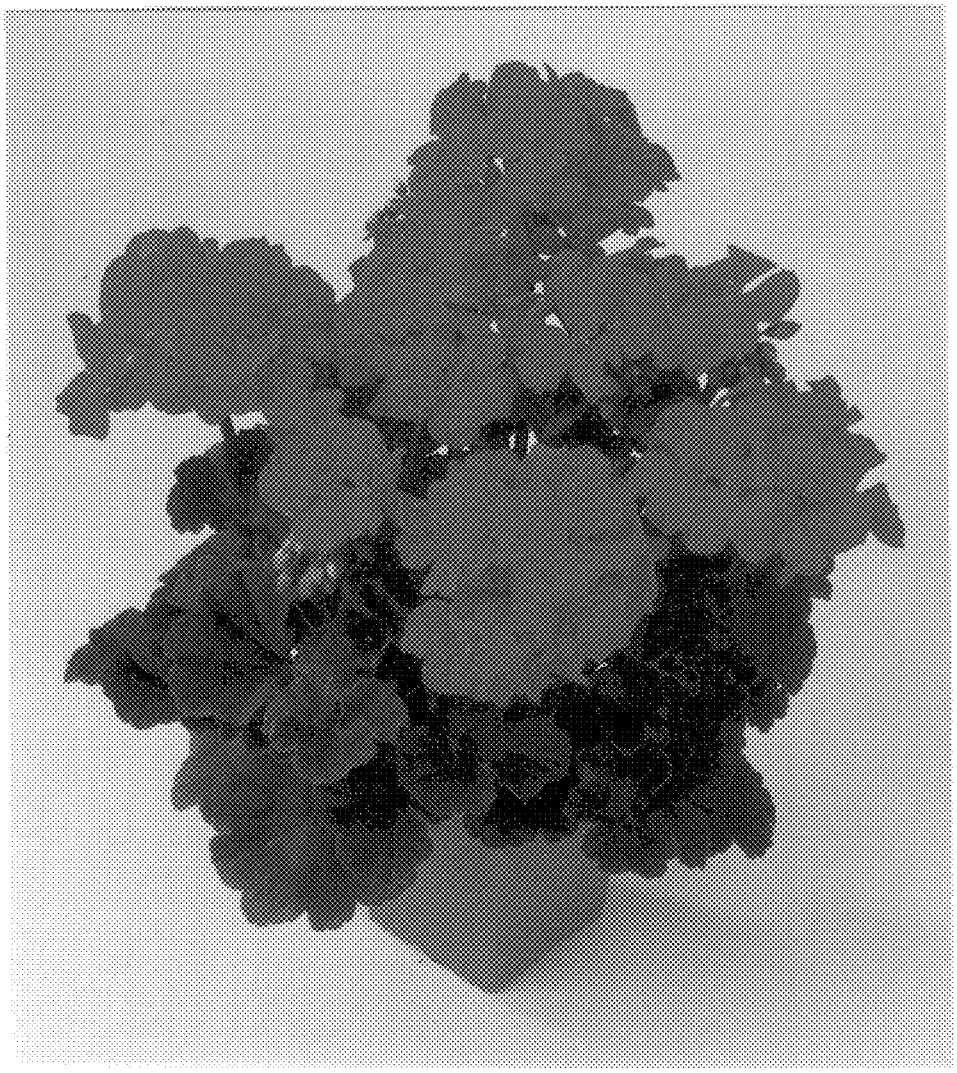

* * * * *